US00PP20784P2

(12) United States Plant Patent
Ikeda et al.

(10) Patent No.: US PP20,784 P2
(45) Date of Patent: Feb. 23, 2010

(54) ***FUCHSIA* PLANT NAMED 'SANIFHOHO'**

(50) Latin Name: *Fuchsia×hybrida*
Varietal Denomination: Sanifhoho

(75) Inventors: Mito Ikeda, Hyogo (JP); Yasuo Kishimoto, Hyogo (JP); Hidefumi Funakoshi, Hyogo (JP); Yasuyuki Murakami, Shiga (JP)

(73) Assignees: Suntory Flowers Limited, Tokyo (JP); Nishinomiya City, Hyogo (JP)

( * ) Notice: Subject to any disclaimer, the term of this patent is extended or adjusted under 35 U.S.C. 154(b) by 0 days.

(21) Appl. No.: 12/290,136

(22) Filed: Oct. 28, 2008

(51) Int. Cl.
*A01H 5/00* (2006.01)

(52) U.S. Cl. ..... Plt./300

(58) Field of Classification Search ..... Plt./300
See application file for complete search history.

*Primary Examiner*—Susan B McCormick Ewoldt
(74) *Attorney, Agent, or Firm*—C. A. Whealy

(57) ABSTRACT

A new and distinct cultivar of *Fuchsia* plant named 'Sanifhoho', characterized by its compact and mounding growth habit; freely branching and bushy plant habit; white-colored flowers; freely flowering habit; long flowering period; and relative tolerance to low and high temperatures.

1 Drawing Sheet

Botanical designation: *Fuchsia×hybrida.*
Cultivar denomination: 'Sanifhoho'.

BACKGROUND OF THE INVENTION

The present invention relates to a new and distinct cultivar of *Fuchsia*, botanically known as *Fuchsia×hybrida* and hereinafter referred to by the name 'Sanifhoho'.

The new *Fuchsia* plant is a product of a planned breeding program conducted by the Inventors in Nishinomiya, Hyogo, Japan. The objective of the breeding program is to create new mounding and freely branching *Fuchsia* cultivars with numerous flowers and attractive flower color.

The new *Fuchsia* plant originated from a cross-pollination made by the Inventors in 2003 in Nishinormiya, Hyogo, Japan of a proprietary selection of *Fuchsia×hybrida* identified as code number auf2, not patented, as the female, or seed, parent with a proprietary selection of *Fuchsia×hybrida* identified as code number ark6, not patented, as the male, or pollen, parent. The new *Fuchsia* was discovered and selected by the Inventor as a single flowering plant within the progeny of the stated cross-pollination in a controlled greenhouse environment in Nishinomiya, Hyogo, Japan in October, 2005.

Asexual reproduction of the new *Fuchsia* plant by terminal cuttings in a controlled environment in Nishinomiya, Hyogo, Japan and Higashiomi, Shiga, Japan since November, 2005, has shown that the unique features of this new *Fuchsia* plant are stable and reproduced true to type in successive generations.

SUMMARY OF THE INVENTION

Plants of the new *Fuchsia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Saniflioho'.

These characteristics in combination distinguish 'Saniflioho' as a new and distinct cultivar of *Fuchsia:*

1. Compact and mounding growth habit.
2. Freely branching and bushy plant habit.
3. White-colored flowers.
4. Freely flowering habit; long flowering period.
5. Relatively tolerant to low and high temperatures.

Plants of the new *Fuchsia* differ primarily from plants of the female parent selection in the following characteristics:

1. Plants of the new *Fuchsia* have larger leaves than plants of the female parent selection.
2. Plants of the new *Fuchsia* and the female parent selection differ in flower color as plants of the female parent selection have purple violet and light pink bi-colored flowers.

Plants of the new *Fuchsia* differ primarily from plants of the male parent selection in the following characteristics:

1. Plants of the new Petunia are more mounding than and not as upright as plants of the male parent selection.
2. Plants of the new *Fuchsia* have green-colored stems whereas plants of the male parent selection have red purple-colored stems.
3. Plants of the new *Fuchsia* have single flowers whereas plants of the male parent selection have double flowers.

Plants of the new *Fuchsia* can also be compared to plants of 'Sanihanf arl2' disclosed in U.S. Plant Pat. No. 16,779. In side-by-side comparisons conducted in Nishinomiya, Hyogo, Japan, plants of the new *Fuchsia* and 'Sanihanf arl2' differed in the following characteristics:

1. Plants of the new *Fuchsia* had shorter lateral branches than plants of 'Sanihanf arl2'.
2. Plants of the new *Fuchsia* had smaller leaves than plants of 'Sanihanf arl2'.
3. Plants of the new *Fuchsia* had larger flowers than plants of 'Sanihanf arl2'.
4. Plants of the new *Fuchsia* and 'Sanihanf arl2' differed in petal color as plants of 'Sanihanf arl2' had red purple and white bi-colored petals.

BRIEF DESCRIPTION OF THE PHOTOGRAPHS

The accompanying colored photographs illustrate the overall appearance of the new *Fuchsia*, showing the colors as true as it is reasonably possible to obtain in colored reproductions of this type. Colors in the photographs may differ slightly from the color values cited in the detailed botanical description which accurately describe the colors of the new *Fuchsia*.

The photograph at the top of the sheet comprises a side perspective view of a typical flowering plant of 'Sanifhoho' grown in a container.

The photograph at the bottom of the sheet is a close-up of a typical flower and flower buds of 'Sanifhoho'.

DETAILED BOTANICAL DESCRIPTION

The aforementioned photographs and following observations, measurements and values describe plants grown in Nishinomiya, Hyogo, Japan, under commercial practice in a polyethylene-covered greenhouse with day temperatures ranging from 15° C. to 32° C. and night temperatures ranging from 10° C. to 25° C. Plants had been growing for about one year in 13.5-cm containers when the description and photographs were taken. In the following description, color references are made to The Royal Horticultural Society Colour Chart, 2001 Edition, except where general terms of ordinary dictionary significance are used.

Botanical classification: *Fuchsia×hybrida* 'Sanifhoho'.

Parentage:

*Female, or seed, parent.*—Proprietary selection of *Fuchsia×hybrida* identified as code number auf2, not patented.

*Male, or pollen, parent.*—Proprietary selection of *Fuchsia×hybrida* identified as code number ark6, not patented.

Propagation:

*Type.*—By terminal cuttings.

*Time to initiate roots, summer.*—About one to two weeks at temperatures of 20° C. to 25° C.

*Time to initiate roots, winter.*—About two to three weeks at temperatures of 15° C. to 23° C.

*Time to produce a rooted young plant, summer.*—About three weeks at temperatures of 20° C. to 25° C.

*Time to produce a rooted young plant, winter.*—About 30 days at temperatures of 15° C. to 23° C.

*Root description.*—Fine, fibrous; yellowish white in color.

*Rooting habit.*—Freely branching; moderately dense.

Plant description:

*Plant and growth habit.*—Compact and mounding plant habit. Freely branching; with lateral branches developing potentially at every node; bushy plant habit; vigorous growth habit.

*Plant height.*—About 30 cm.

*Plant diameter.*—About 25 cm.

Lateral branch description:

Length.—About 12 cm.

*Diameter.*—About 2.1 mm.

*Internode length.*—About 2.8 cm.

*Strength.*—Strong.

*Aspect.*—Initially upright to outwardly arching.

*Texture.*—Pubescent.

*Color.*—Close to 146D; occasionally lightly tinted with close to 59A.

Foliage description:

*Arrangement.*—Opposite, simple.

*Length.*—About 5.5 cm.

*Width.*—About 2.9 cm.

*Shape.*—Ovate.

*Apex.*—Acute.

*Base.*—Obtuse.

*Margin.*—Entire.

*Texture, upper and lower surfaces.*—Sparsely pubescent.

*Venation pattern.*—Pinnate; reticulate.

Color.—Developing leaves, upper surface: Close to 137C. Developing leaves, lower surface: Close to 138B. Fully expanded leaves, upper surface: Close to 137B; venation, close to 137B. Fully expanded leaves, lower surface: Close to 146A; venation, close to 146A.

*Petiole.*—Length: About 10.9 mm. Diameter: About 1.9 mm. Texture, upper and lower surfaces: Smooth, glabrous. Color, upper and lower surfaces: Close to 146D tinted with close to 59A.

Flower description:

*Flower arrangement and habit.*—Single axillary flowers; flowers pendulous. Freely flowering habit with potentially two flowers per leaf axil.

*Fragrance.*—None detected.

*Natural flowering season.*—Long flowering period; in Japan, plants flower from spring to autumn; flowering continuous during this period.

*Flower longevity.*—Flowers last about three to four days on the plant; flowers not persistent.

*Flower diameter.*—About 5.8 cm.

*Flower height (depth).*—About 3.3 cm.

*Flower buds.*—Shape: Lenticular. Length: About 3.5 cm. Diameter: About 1.4 cm. Color: Close to N155B.

*Petals.*—Arrangement: Typically four in a single whorl. Length: About 2.2 cm. Width: About 2.4 cm. Shape: Obovate. Apex: Truncate. Base: Obtuse. Margin: Entire. Texture, upper and lower surfaces: Smooth, glabrous; satiny. Color: When opening, upper and lower surfaces: Close to N155B. Fully opened, upper and lower surfaces: Close to N155B.

*Sepals.*—Arrangement: Calyx star-shaped with four sepals fused at the base. Length: About 3.4 cm. Width: About 1.1 cm. Shape: Oblong. Apex: Acuminate. Base: Obtuse. Margin: Entire. Texture, upper and lower surfaces: Smooth, glabrous; satiny. Color: When opening and fully opened, upper surface: Close to N155B. When opening and fully opened, lower surface: Close to N155B; blushed with pink.

*Peduncles.*—Length: About 3.6 cm. Diameter: About 0.8 mm. Angle: Arching. Strength: Moderately strong. Texture: Sparsely pubescent. Color: Close to 145B.

*Reproductive organs.*—Stamens: Quantity: Eight per flower. Anther shape: Ellipsoidal. Anther size: About 5 mm by 1.8 mm. Anther color: Close to 60D. Pollen amount: Moderate. Pollen color: Close to 155A. Pistils: Quantity: One per flower. Pistil length: About 6.5 cm. Style color: Close to 155C; towards the apex, close to 69C. Stigma shape: Conical. Stigma color: Close to 10D. Ovary color: Close to 144A.

*Seed/fruit.*—Seed and fruit development have not been observed on plants of the new *Fuchsia*.

Temperature tolerance: Plants of the new *Fuchsia* have relatively good temperature tolerance and have been observed to tolerate temperatures ranging from about −2° C. to about 33° C.

Pathogen/pest resistance: Plants of the new *Fuchsia* have not been observed to be resistant to pests and pathogens common to *Fuchsia*.

It is claimed:

1. A new and distinct *Fuchsia* plant named 'Sanifhoho' as illustrated and described.

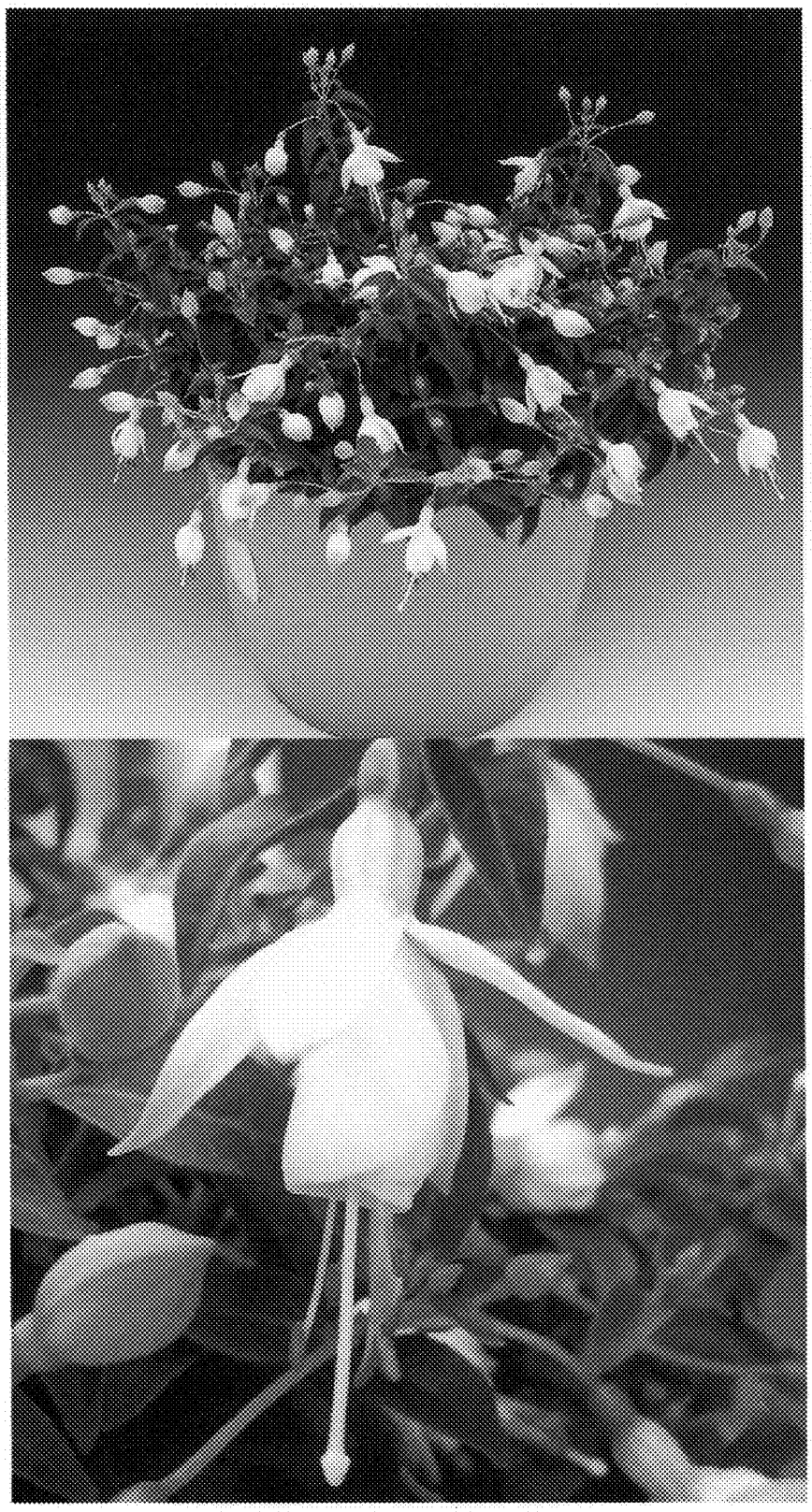

* * * * *